US00PP27518P2

(12) United States Plant Patent
Delabroye

(10) Patent No.: US PP27,518 P2
(45) Date of Patent: Dec. 27, 2016

(54) ***HEUCHERA* PLANT NAMED 'FAIRY DANCE 2'**

(50) Latin Name: ***Heuchera* hybrid**
Varietal Denomination: Fairy Dance 2

(71) Applicant: Thierry Delabroye, Hantay (FR)

(72) Inventor: Thierry Delabroye, Hantay (FR)

(73) Assignee: SANDRINE DELABROYE, Hantay (FR)

( * ) Notice: Subject to any disclaimer, the term of this patent is extended or adjusted under 35 U.S.C. 154(b) by 88 days.

(21) Appl. No.: 14/544,155

(22) Filed: Dec. 3, 2014

(51) Int. Cl.
*A01H 5/12* (2006.01)

(52) U.S. Cl.
USPC ..... Plt./440

(58) Field of Classification Search
USPC ..... Plt./440
See application file for complete search history.

(56) References Cited

PUBLICATIONS

Glick's Greenhouse facebook, 1 Quart Perennials—2013 Availability (While Supplies Last), retrieved on Apr. 25, 2016, retrieved from the Internet at <https://www.facebook.com/notes/glicks-greenhouse/1-quart-perennials-2013-availability-while-supplies-last/645390085486563/> 5 pp.*

Florexpo 2012-2013 catalog, retrieved on Sep. 14, 2016, retrieved from the Internet at <https://issuu.com/cairodoutcher/docs/florexpo-catalog-perennials-2013> pp. 3 and 19.*

* cited by examiner

*Primary Examiner* — June Hwu
(74) *Attorney, Agent, or Firm* — Penny J. Aguirre

(57) ABSTRACT

A new cultivar of hybrid *Heuchera* named 'Fairy Dance 2', characterized by its foliage that is tri-colored with slivery grey centers, bright green margins, and brown surrounding veins, its compact plant habit with a tight mound of foliage, its abundance of flowering stems, and its pink-red flowers on tall red flowering stems.

2 Drawing Sheets

Botanical classification: *Heuchera* hybrid.
Cultivar designation: 'Fairy Dance 2'.

BACKGROUND OF THE INVENTION

The present invention relates to a new and distinct cultivar of *Heuchera* of hybrid origin, botanically known as a *Heuchera* and is hereinafter referred to by its cultivar name 'Fairy Dance 2'.

The new cultivar was discovered as a whole plant mutation in a trial field by the Inventor in Hantay, France in June of 2011. The trial field contained hundreds of cultivars and proprietary seedlings of *Heuchera* from the Inventor's breeding program. The parentage of 'Fairy Dance 2' is therefore unknown.

Asexual propagation of the new cultivar was first accomplished under the direction of the Inventor by in vitro propagation using meritstem tissue in Paraiso, Costa Rica in June 2012. Asexual propagation of the new cultivar by stem cuttings and in vitro propagation has shown that the unique features are stable and reproduced true to type in successive generations.

SUMMARY OF THE INVENTION

The following traits have been repeatedly observed and represent the characteristics of the new cultivar. These attributes in combination distinguish 'Fairy Dance 2' as a new and unique cultivar of *Heuchera*.

1. 'Fairy Dance 2' exhibits foliage that is tri-colored with silvery grey centers, bright green margins, and brown surrounding veins.

2. 'Fairy Dance 2' exhibits a compact plant habit with a tight mound of foliage.
3. 'Fairy Dance 2' exhibits pink-red flowers on tall red flowering stems.

'Fairy Dance 2' can be most closely compared to the Heuchera cultivars 'Silver Blush' (U.S. Plant Pat. No. 25,329) and 'Silver Light' (U.S. Plant Pat. No. 15,067). Both are similar to 'Fairy Dance 2' in plant habit and in having silver foliage. 'Silver Blush' differs from 'Fairy Dance 2' in having leaves that are bi-colored with silver centers, no distinct margins, and red-brown veins that mature to grey green. 'Silver Light' differs from 'Fairy Dance 2' in having leaves that are metallic silver in color with dark grey green veins with a lower surface that is red-purple in color and in having flowers that are light pink in color.

BRIEF DESCRIPTION OF THE DRAWINGS

The accompanying colored photographs illustrate the overall appearance and distinct characteristics of the new *Heuchera*. The photographs were taken of plants six months in age as grown in a 5.9-liter container in an unheated greenhouse in Noordwijkerhout, The Netherlands (4 plugs per container).

The photograph in FIG. 1 provides a side view of the plant habit of 'Fairy Dance 2' in bloom.

Figure 1:
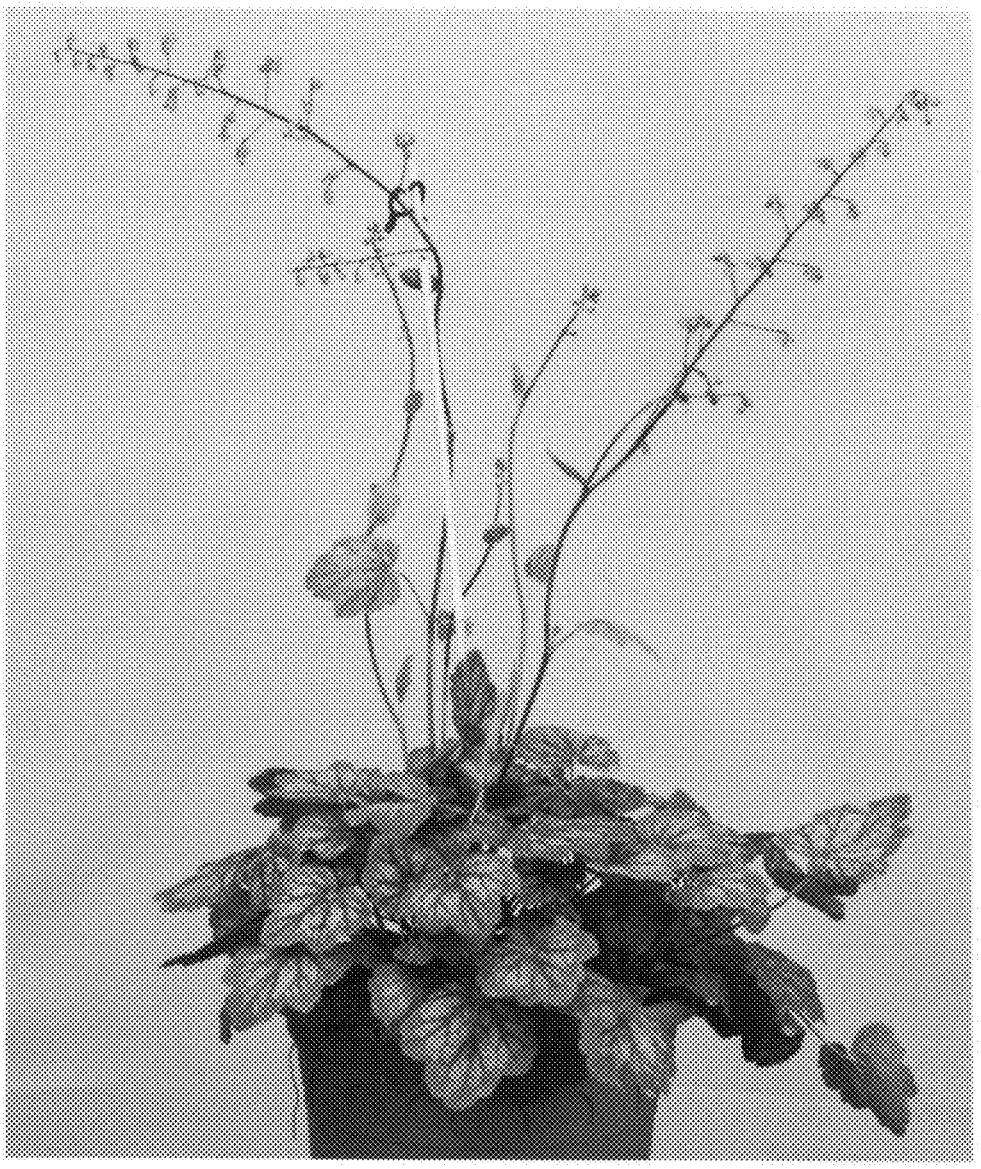
Figure 2:
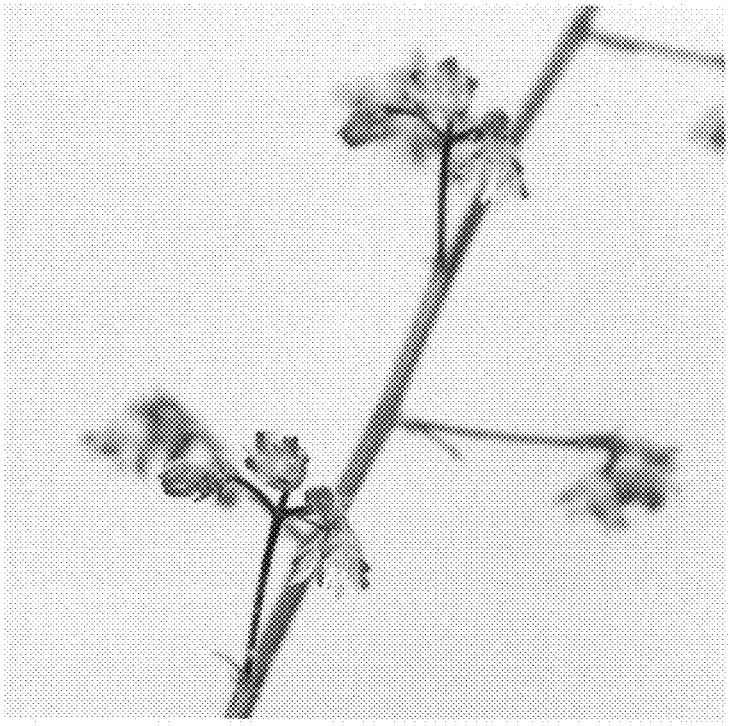

The photograph in FIG. 2 provides a close-up view of the flowers of 'Fairy Dance 2'.

Figure 3:
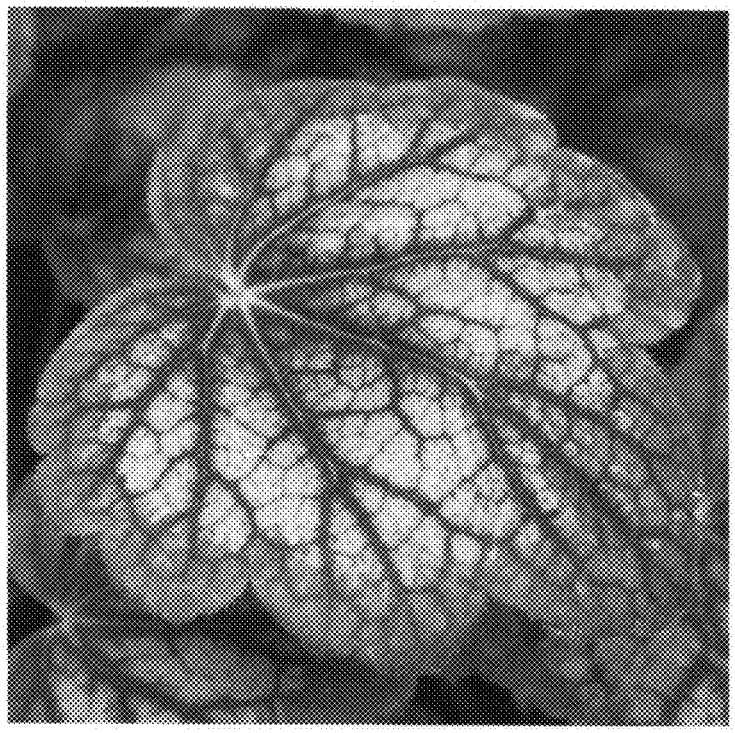

The photograph in FIG. 3 provides a close-up view of a leaf of 'Fairy Dance 2'.

The colors in the photographs are as close as possible with the digital photography techniques available, the color values cited in the detailed botanical description accurately describe the colors of the new *Heuchera*.

DETAILED BOTANICAL DESCRIPTION OF THE PLANT

The following is a detailed description of plants six months in age as grown in 5.9-liter containers in an unheated greenhouse in Noordwijkerhout, The Netherlands (4 plugs per container). The phenotype of the new cultivar may vary with variations in environmental, climatic, and cultural conditions, as it has not been tested under all possible environmental conditions. The color determination is in accordance with The 2007 R.H.S. Colour Chart of The Royal Horticultural Society, London, England, except where general color terms of ordinary dictionary significance are used.

General description:

*Blooming period*.—Late spring into summer in The Netherlands.

*Plant type*.—Herbaceous perennial.

*Plant habit*.—Compact, clump-forming, mounded foliage, tall flowering scapes.

*Height and spread*.—Average of 17 cm in height from soil to top of leaves and 70 cm from soil to top of inflorescences and 30 cm in width (4 plugs in a 5.9-liter container).

*Hardiness*.—At least in U.S.D.A. Zones 3 to 9.

*Diseases and pests*.—No particular susceptibility or resistance to pests or diseases has been observed.

*Environmental stresses*.—Tolerant to heat and humidity.

*Root description*.—Fibrous roots on woody rootstalks.

*Root development*.—A tissue culture plug will fully develop in a 7-cm container in about 13 weeks.

*Branching habit*.—Flowering stem emerge from basal rosettes, no lateral branches.

*Propagation*.—In vitro propagation preferred, stem cuttings and division are also possible.

*Growth rate*.—Moderate.

Stem description (peduncle, flowering stem):

*Shape*.—Round.

*Stem color*.—A blend of 178A.

*Stem size*.—An average of 3 mm in diameter and 67.9 cm in length.

*Stem strength*.—Moderately strong.

*Stem aspect*.—Flowering stems grow in an average angle of 75° to base (0°=horizontal).

*Stem surface*.—Moderately glossy, densely covered with short soft hairs, average of 0.05 cm in length, NN155D in color.

*Stem number*.—Average of 6 per 5.9-liter container.

Foliage description:

*Leaf shape*.—Broad ovate to near orbicular.

*Leaf division*.—Simple.

*Leaf base*.—Hastate, free to touching.

*Leaf apex*.—Obtuse.

*Leaf venation*.—Laciniate, upper vein color; 144B, lower vein color; 147D.

*Leaf margins*.—Lobed with shallow indentations with average of 7 lobes per leaf, margins crenate with weak undulation.

*Leaf attachment*.—Petiolate.

*Leaf arrangement*.—Alternate, basal rosettes.

*Leaf orientation*.—Typically nearly horizontal to petiole.

*Leaf surface*.—Upper surface matte and sparsely pubescent, lower surface very slightly glossy and sparsely pubescent on veins, hairs are very short strigose hairs an average of 0.75 mm in length and NN155D in color.

*Leaf color*.—Young upper surface; 147C, margins 143A to 143B, areas along the main veins, secondary and tertiary veins 200C, young lower surface; 147C, areas along the main veins, secondary and tertiary veins 197B to 197C, mature upper surface; ranging between 138D and 193A, margins 143A, areas along the main veins, secondary and tertiary veins in between N137D and 147A, mature lower surface; 147C, areas along the main veins, secondary and tertiary veins slightly tinged 197C to 197D.

*Leaf size*.—Average of 8 cm in length and 7.8 cm in width.

*Leaf quantity*.—33 per basal rosette.

*Petioles*.—Average of 14 cm in length and 2 mm in width, color in between 148A and 195A, tinged towards the base 177D, surface texture finely pubescent.

*Stipules*.—Small leafy stipules at the base of each leaf, narrow acute apex, base truncate, with an average of 1.2 cm in length and 2.5 mm in width, color; 145C, surface finely pubescent on both surfaces.

Flower description:

*Inflorescence type*.—Numerous small bell-shaped flowers arranged on pyramidal panicles on flower scapes emerging from the base of the rosette.

*Inflorescence size*.—An average of 30.5 cm in height (excluding peduncle) and 9.9 cm in width.

*Inflorescence number*.—1 per flowering stem.

*Flower fragrance*.—None.

*Flower quantity*.—Average of 80 flowers per inflorescence, medium density.

*Flower lastingness*.—Average of one week.

*Flower buds*.—Obovate in shape, an average of 5 mm in length and 3 mm in diameter, 51A in color.

*Flower aspect*.—Outward to slightly nodding.

*Flower type*.—Campanulate.

*Flower size*.—About 8 mm in length and 7 mm in diameter.

*Petals*.—Average of 5, rotate arrangement with base implanted in the hypanthium, narrow rhomboidal to narrow obovate in shape, margin is serrate, apex is acute, upper and lower surface is matte and smooth, color of upper and lower surface when opening and fully open; 63C.

*Calyx*.—Campanulate, sepals fused to hypanthium, 7 mm in length and diameter.

*Sepals*.—5, fused, campanulate hypanthium, elliptic in shape, average of 7 mm in length and 2.5 mm in width, margin is entire, apex is broadly acute, fused base, both surfaces are matte, lower side is moderately covered with very short glandular hairs 0.025 cm in length and 69D in color, color: immature upper surface; 61D, base 75C, immature lower surface; between N57C and 58C, tips 59B, base 153A, mature upper surface; 61D, base 75C, mature lower surface; between N57C and 58C, tips 59B, base 153A.

*Bracts*.—1, at base of petioles, lanceolate in shape, 178A in color on both surfaces, about 3 mm in length and 0.7 mm in width, acute apex, base truncate, surface slightly pubescent on both surfaces.

*Pedicels*.—Average of 3 mm in length and 0.5 mm in width, 181A in color, moderate strength, average angle of 45° (0°=straight on top of secondary peduncle), surface slightly pubescent.

Reproductive organs:

*Gynoecium*.—2 pistils, 5 mm in length, stigma is pointed and 157B in color, styles are 4 mm in length and 155A in color, ovaries are 157D in color.

*Androcoecium*.—About 5 stamens, anthers are ovate in shape, about 0.5 mm in length and 155A in color, filament 3 mm in length and NN155C in color, pollen is low in quantity and 156A in color.

*Seed/fruit*.—No fruit or seeds were observed to date.

It is claimed:

1. A new and distinct cultivar of hybrid *Heuchera* plant named 'Fairy Dance 2' as herein illustrated and described.

* * * * *